(12) United States Patent
Ganesan

(10) Patent No.: US 7,564,240 B2
(45) Date of Patent: Jul. 21, 2009

(54) METHOD AND APPARATUS FOR MEASURING FREE INDUCTION DECAY SIGNAL AND ITS APPLICATION TO COMPOSITION ANALYSIS

(75) Inventor: Krishnamurthy Ganesan, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 19 days.

(21) Appl. No.: 11/765,237

(22) Filed: Jun. 19, 2007

(65) Prior Publication Data

US 2008/0315873 A1    Dec. 25, 2008

(51) Int. Cl.
*G01V 3/00*    (2006.01)
(52) U.S. Cl. .................................................. 324/303
(58) Field of Classification Search .......... 324/300–322
See application file for complete search history.

(56) References Cited

U.S. PATENT DOCUMENTS

| | | | |
|---|---|---|---|
| 5,055,787 A | | 10/1991 | Kleinberg et al. |
| 5,291,137 A | * | 3/1994 | Freedman ................... 324/303 |
| 5,486,742 A | | 1/1996 | Chino et al. |
| 5,486,762 A | * | 1/1996 | Freedman et al. ........... 324/303 |
| 5,796,252 A | * | 8/1998 | Kleinberg et al. ............ 324/303 |
| 6,166,543 A | * | 12/2000 | Sezginer et al. ............. 324/303 |
| 6,369,567 B1 | * | 4/2002 | Song et al. ................... 324/303 |
| 6,452,389 B1 | * | 9/2002 | Edwards ..................... 324/303 |
| 6,559,640 B2 | | 5/2003 | Taicher ....................... 324/303 |
| 6,845,262 B2 | * | 1/2005 | Albert et al. ................. 600/420 |
| 6,882,147 B2 | * | 4/2005 | Taicher et al. ............... 324/303 |
| 7,036,362 B2 | | 5/2006 | Haddad et al. |
| 7,205,762 B2 | * | 4/2007 | Blanz et al. ................. 324/303 |

* cited by examiner

*Primary Examiner*—Brij B. Shrivastav
*Assistant Examiner*—Dixomara Vargas
(74) *Attorney, Agent, or Firm*—Darla P. Fonseca; Jaime Csatano; Dale Gaudier

(57) ABSTRACT

A method to obtain a free induction decay signal using includes inducing a static magnetic field in a sample volume. A radio frequency (RF) magnetic field is then induced in the sample volume. The RF magnetic field has parameters selected to minimize the contribution of inhomogeneity in the static magnetic field to a free induction decay time. The free induction decay signal is then detected from the sample volume. In one example, prior to inducing the RF magnetic field, a reorienting radio frequency magnetic field is induced in the sample volume to reorient magnetic spins by a first selected angle. The inducing the RF magnetic field in this example has parameters selected to reorient spins by a second angle. The inducing the RF magnetic field and detecting the free induction decay signal are repeated until nuclear magnetic equilibrium is substantially attained.

19 Claims, 7 Drawing Sheets

METHOD AND APPARATUS FOR MEASURING FREE INDUCTION DECAY SIGNAL AND ITS APPLICATION TO COMPOSITION ANALYSIS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The invention relates generally to the field of nuclear magnetic resonance ("NMR") measurement of subsurface formations penetrated by a wellbore. More specifically, the invention relates to methods and apparatus for measuring NMR free induction decay signals using wellbore deployed instruments, and the use of such free induction decay signals in determining NMR properties of the formation.

2. Background Art

NMR instruments used to make measurements of NMR properties of subsurface Earth formations, called "well logging" tools or instruments are moved along the interior of a wellbore drilled through such formations. NMR well logging devices known in the art include one described in U.S. Pat. No. 5,055,787 issued to Kleinberg et al. and assigned to the assignee of the present invention. As a general principle, the instrument disclosed in the '787 patent makes measurements by inducing a strong, substantially homogeneous static magnetic field B in a volume of an adjacent subsurface formation on one side of the instrument to measure nuclear magnetic resonance characteristics thereof. The instrument has a radio frequency ("RF") antenna mounted on the outside of a metal body of the instrument, directing focused oscillating RF magnetic fields at the volume to tip the magnetic moments of hydrogen nuclei of fluids within pore spaces in the subsurface formations. The same antenna can be used to receive signals of proton precession emanating from within the volume of interest after transmission of the RF polarizing field. Rapid damping of the antenna energy between the transmitting and receiving modes of operation is accomplished by a Q-switch. The disclosed instrument provides for the direct measurement of NMR signal decay having transverse relaxation time (T2) behavior, and further provides for the fast repetition of pulsed measurements from within a wellbore. An additional magnet array may be mounted offset from the first magnet configuration to prepolarize a formation before it is measured in order to pre-align a larger number of hydrogen nuclei than a single magnet configuration could do by itself.

The instrument described in the '787 patent, as is the case for other NMR well logging instruments known in the art, makes measurements of transverse relaxation time properties of the subsurface formations using a pulsing sequence known as Carr-Purcell-Meiboom-Gill ("CPMG"), or modifications of the CPMG sequence. The CPMG sequence is initiated after hydrogen nuclei are prepolarized along the direction of the static magnetic field by applying an RF field having frequency substantially equal to the Larmor frequency of the hydrogen nuclei, and amplitude and duration selected to reorient the nuclear magnetic spin axes of the hydrogen nuclei to be transverse to the static magnetic field direction (called a 90 degree pulse). Proton spin precession about the static magnetic field direction induces signals in the RF antenna that are detected by the instrument and called the Free Induction Decay (FID). Over a period of time, the nuclear magnetic spins of the hydrogen nuclei become out of phase with each other, such that the detected RF magnetic field signal decays substantially to zero. After a selected time interval, a series of "refocusing" pulses is applied. The refocusing pulses have duration and amplitude selected to invert the spin phasing of the hydrogen nuclei so that eventually the proton precession will come back in phase. When the proton precession comes back in phase, an RF signal is induced in the RF antenna and is detected. Such signal generation and detection is referred to as "spin echo" detection. The refocus pulsing and RF spin echo signal detection is repeated for a selected number of pulses. Each successive spin echo is reduced in amplitude from the preceding one. The rate at which the spin echo amplitude decays is related to the transverse relaxation time ($T_2$) properties of the various fluids in the subsurface formations. Analysis of the fluids in the formation may be performed by analyzing the multicomponent exponential decay of the amplitudes of successive spin echoes. A result of such analysis is a $T_2$ distribution of the various hydrogen-bearing fluids in the subsurface formations. Such distribution may be related to the petrophysical properties of the formations.

If a pure FID signal is measured, the same analysis can be applied to the FID signal. The FID signal can be correlated to useful information, such as the fractional volume of fluid filled pore spaces (porosity) in the subsurface formations. Notwithstanding that the above mentioned NMR apparatus induces a substantially homogeneous static magnetic field in the formations, there is still some inhomogeneity in the static magnetic field. Such inhomogeneity is an essentially unavoidable result of "inside out" NMR apparatus such as well logging instruments, wherein the volume of investigation is entirely outside the apparatus. The inhomogeneity of the static magnetic field has the effect of shortening the FID signal decay time so that its measurement becomes impracticable. Also it is difficult to design a magnet for application with well logging instruments having a magnetic field within a few parts per million (ppm) homogeneity within the investigated regions.

Another NMR property of interest is the longitudinal ($T_1$) relaxation time. Techniques known in the art for measuring $T_1$ of subsurface formations include a technique that determines a $T_1/T_2$ ratio using multiple waiting times between successive CPMG sequences. Such technique is described in U.S. Pat. No. 5,486,742 issued to Freedman et al. and assigned to the assignee of the present invention. A characteristic common to $T_1$ determination techniques known in the art is that multiple pulse sequences are used, whether having a single wait time between sequences or otherwise. The length of time to acquire such sequences has the practical effect of limiting the speed at which the well logging instruments can be moved through the wellbore.

There exists a need for techniques that enable measurement of the FID signal by an NMR well logging instrument, and techniques to increase the effective logging speed while measuring $T_1$ properties of the subsurface formation.

SUMMARY OF THE INVENTION

A method to obtain a free induction decay signal using a downhole logging tool according to one aspect of the invention includes inducing a static magnetic field in a sample volume. A radio frequency magnetic field is then induced in the sample volume. The radio frequency magnetic field has parameters selected to minimize the contribution of inhomogeneity in the static magnetic field to a free induction decay time. The free induction decay signal is then detected from the sample volume.

A method for analyzing materials in a sample volume according to another aspect of the invention includes inducing a static magnetic field in the sample volume. A radio frequency magnetic field is induced in the sample volume. The radio frequency magnetic field has parameters selected to reorient nuclear magnetic spins by a first selected angle from alignment with the static magnetic field. A reorienting radio frequency magnetic field is then induced in the sample volume. The reorienting field has parameters selected to reorient magnetic spins by a second selected angle and to minimize contribution of inhomogeneity in the static magnetic field to a free induction decay time. A free induction decay signal is detected from the sample volume. The inducing the reorienting radio frequency magnetic field and detecting the free induction decay signal are repeated until nuclear magnetic equilibrium is substantially attained.

Other aspects and advantages of the invention will be apparent from the following description and the appended claims.

DETAILED DESCRIPTION

Figure 1:
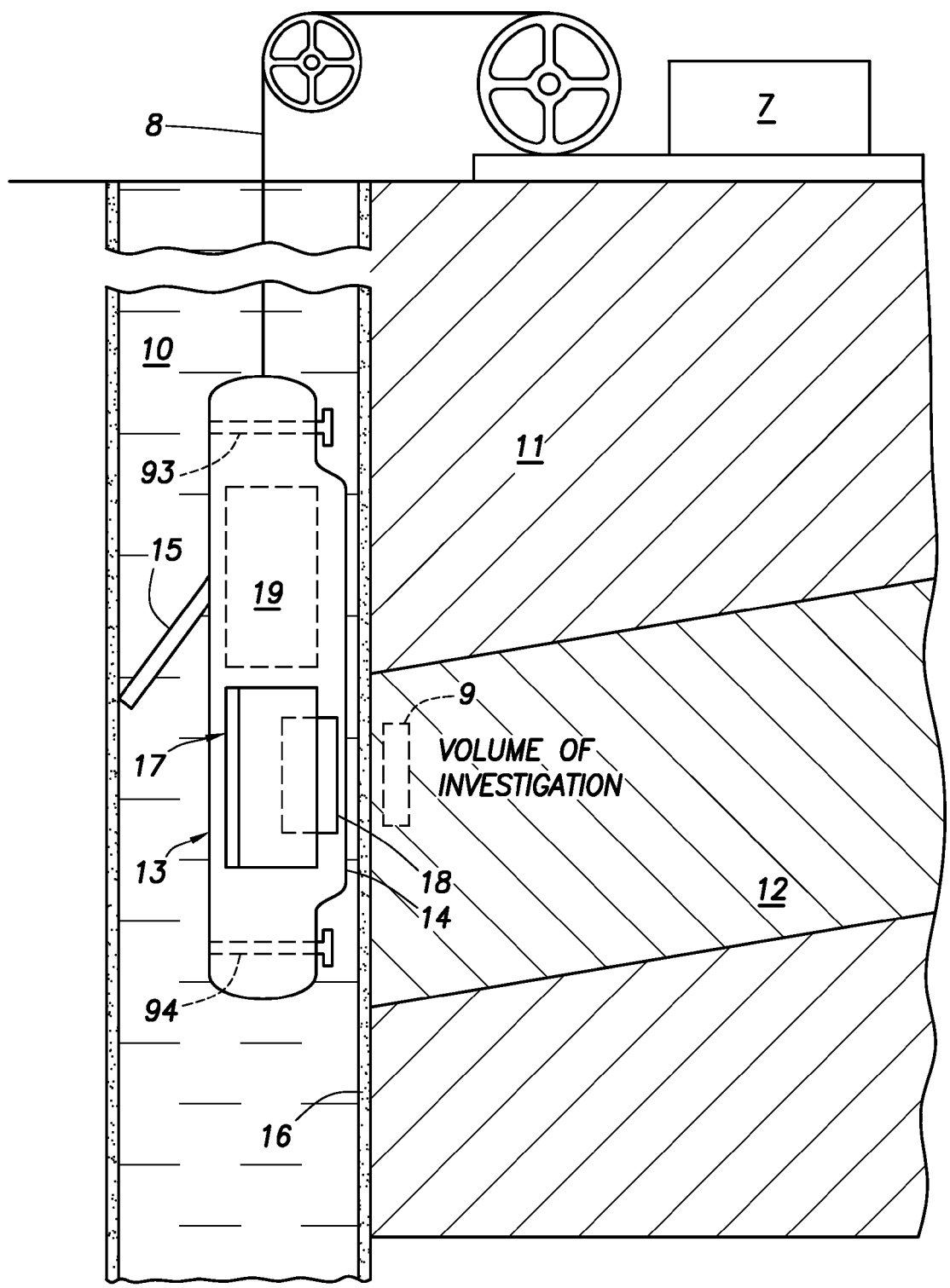
FIG. 1 shows a side view of an example NMR logging instrument positioned in a wellbore for making measurements of surrounding formations, in accordance with the present invention (Prior Art).

FIGS. 1 through 5, described below, are intended to show one example of a NMR well logging instrument that may be used in accordance with the invention. It is to be clearly understood that the various aspects of the present invention are not limited in scope to the implementations shown on such well logging instrument. In FIG. 1 a wellbore 10 is shown penetrating subsurface formations 11, 12, the characteristics of which are to be determined. Within the wellbore 10 there is shown a well logging instrument 13 connected with an armored electrical cable or "wireline" 8 to surface equipment 7. The instrument 13 preferably has a face 14 shaped to contact the wellbore wall with minimal gaps or standoff. The instrument 13 also can have a retractable arm 15 which can be activated to press the body of the instrument 13 against the wellbore wall during operation of the instrument 13, wherein the face 14 is pressed against the wellbore wall.

Although the instrument 13 is shown in FIG. 1 as a single body, the instrument 13 may comprise separate components such as a cartridge, sonde, or skid, and the instrument 13 may be combinable with other well logging instruments as would be apparent to those skilled in the art. Similarly, although the wireline 8 is shown herein as a means for conveyance of the instrument 13 into the wellbore 10 and for communicating signals from the instrument 13 to the surface equipment 7, alternatives are clearly possible. For example, the instrument can be incorporated in a drill string, using forms of telemetry which may not require a cable or wireline.

The formations 11, 12 have distinct characteristics such as mineral composition, porosity, permeability, and fluid content, which can be determined from measurements made by the instrument 13. Deposited upon the wellbore wall of the formations 11, 12 is typically a layer of "mudcake" 16 which is deposited thereon by the natural infiltration of the drilling fluid ("drilling mud") into the formations 11, 12.

In the example shown in FIG. 1, the instrument 13 comprises a magnet array 17 and an antenna 18 positioned between the array 17 and the wall engaging face 14. Magnet array 17 produces a static magnetic field in the wellbore and formations surrounding the instrument 13. The antenna 18 produces, at selected times, an oscillating magnetic field which is directed into formation 12, and is superposed on the static field within those parts of formation opposite the face 14. The volume of investigation 9 of the instrument 13, shown in dotted lines in FIG. 1, is a vertically elongated region directly in front of instrument face 14 in which the magnetic field produced by the magnet array 17 is substantially homogeneous. A prepolarizing magnet 19, shown in dotted lines, may be positioned directly above the magnet array 17 in another example of the instrument 13.

The instrument 13 makes a measurement by magnetically reorienting the nuclear spins of hydrogen nuclei in formation 12 with a pulse of oscillating magnetic field, and then detecting the precession of the reoriented hydrogen nuclei in the static, homogeneous field within the volume of investigation 9, over a period of time. As shown in FIG. 1, the volume of investigation 9 does not overlap the surface of the wall engaging face 14 and does not overlap the mudcake 16 on the wellbore wall.

In a pulse echo type of measurement, as described in the Background section herein, for example, a pulse of RF current is passed through the antenna 18 to generate a pulse of RF field where the RF frequency is selected to excite only hydrogen nuclei subjected to the static magnetic field strength within the volume of investigation 9. The signals induced in the antenna 18 subsequent to the RF pulse represent a measurement of nuclear magnetic precession and decay within the volume of investigation 9, substantially excluding any undesirable contributions from the wellbore fluid, mudcake 16, or portions of the surrounding formations outside the volume of investigation 9.

Circuits (not shown separately) for producing RF power pulses of selected amplitude and duration, and receiver circuits (not shown separately) for detecting and measuring voltages induced in the antenna 18 at selected times may be included in the instrument 13 or in the surface equipment 7, or both.

Figure 2:
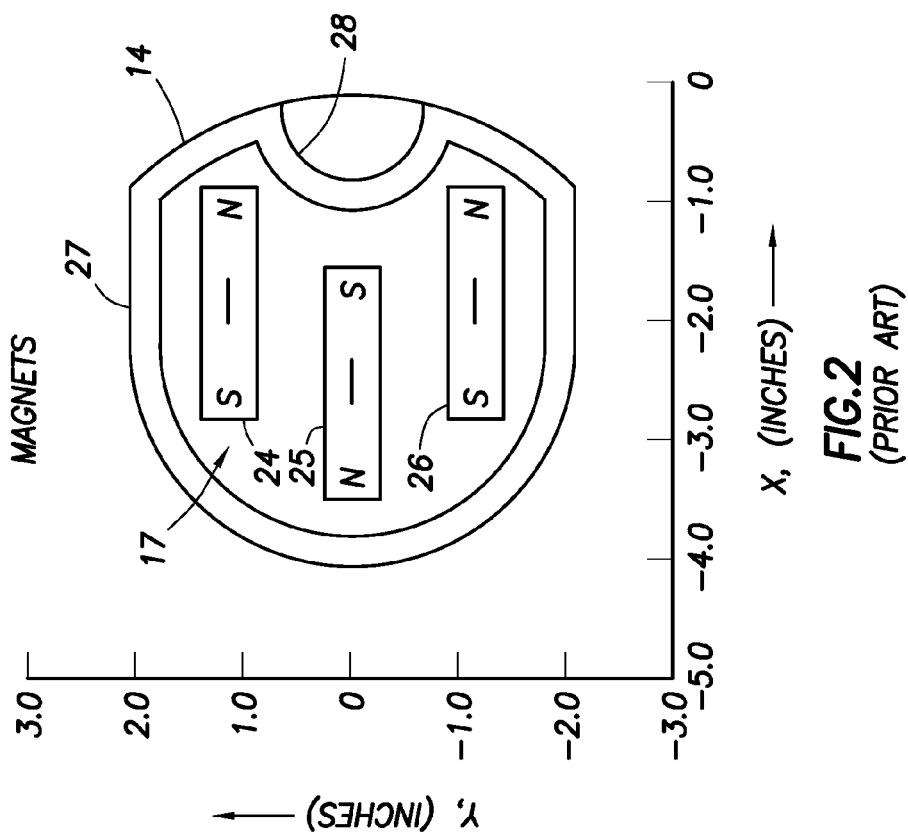
FIG. 2 is an enlarged cross-sectional plan view of a magnet array used in the preferred embodiment of the present invention shown in FIG. 1 (Prior Art).

Referring to FIG. 2, the magnet array 17 can consist of three samarium cobalt permanent magnets 24, 25, 26, which are mounted parallel to each other within a metal alloy body 27. Magnets 24, 25, 26 are elongated in the axial direction of the wellbore, and are 12 inches long in the preferred embodiment. The magnetic poles of the magnets are on the two opposing sides of the magnet and point to the left and right, respectively, in FIG. 2. Thus, within the formation (12 in FIG. 1), the static magnetic field surrounding the magnets remains fairly constant in amplitude along the longitudinal direction of the wellbore axis.

Magnets 24, 25, 26 should be as strong as practical, and should be capable of withstanding physical shock without disintegration. The samarium cobalt magnets that have been used, for example, are preferably enclosed in a sturdy casing such as made from brass to prevent any explosive fragmentations in the event the magnet cracks or breaks. These magnets are commercially available, and have a residual induction of typically 10,500 gauss. It will be appreciated by those skilled in the art that other magnets may be substituted for the samarium cobalt magnets herein, and the magnets can have other dimensions than that shown in the preferred embodiment.

It is preferable to use elongated slab magnets to produce a static field in formation 12 which is constant over a substantial distance L along the z coordinate parallel to the wellbore axis. A large length improves signal to noise ratio and also facilitates continuous well logging measurements along the axis of the wellbore. However, the magnets should not be so long as to make the instrument 13 structurally unwieldy or to cause excessive standoff between the face 14 and the wellbore wall in washed out zones.

Magnets 24, 26 are symmetrically mounted in the two sides of the body 27 with the north poles facing the same directions. Magnet 25 is positioned parallel to and between the other two magnets, but with its north poles facing oppositely from magnets 24, 26. Magnet 25 is also shifted slightly away from face 14, relative to magnets 24, 26. As shown in FIG. 2, the north poles of magnets 24, 26 point in the direction of the face 14 of the instrument, while the north pole of magnet 25 points away from the face 14, although the configuration obviously may be reversed and still produce a similar result.

Figure 5:
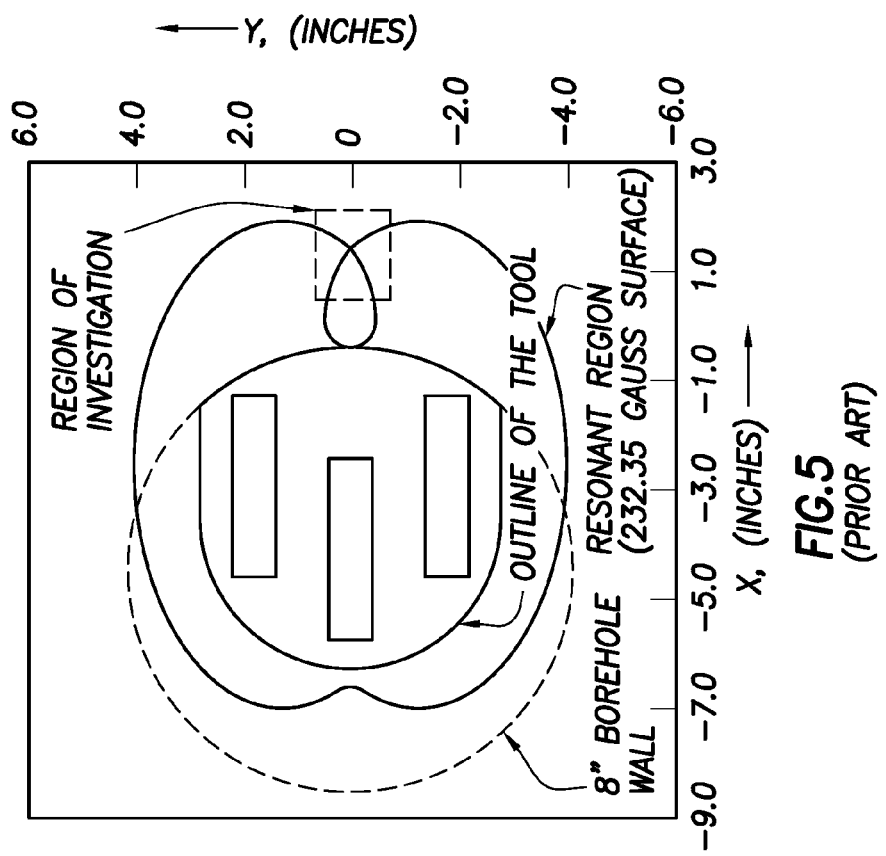
FIG. 5 is a diagram showing a magnetic field equal-magnitude line of 232 gauss, as in FIGS. 2-4, also showing the region of investigation of the preferred embodiment shown in FIG. 1 (Prior Art).
Figure 3:
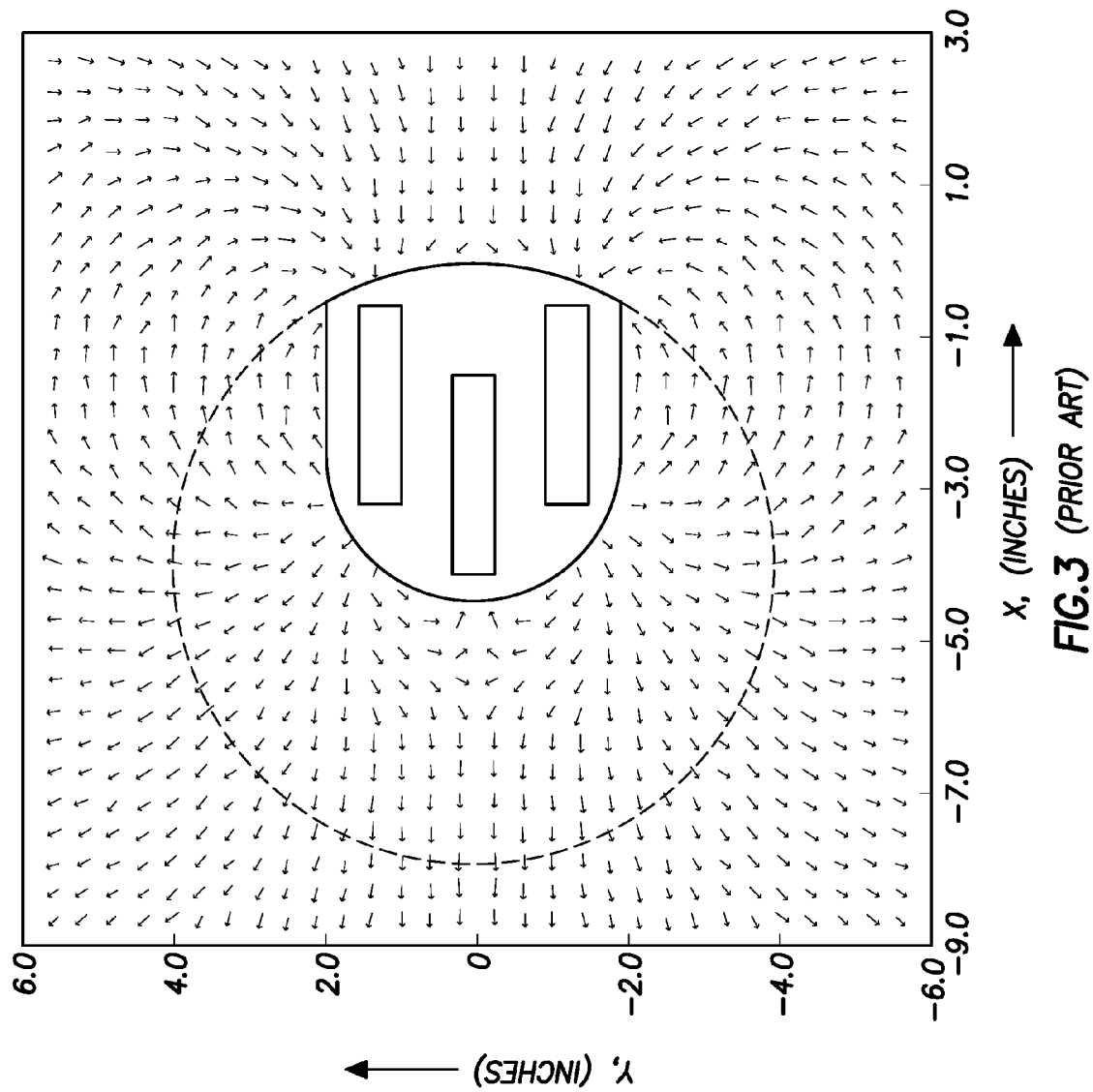
FIG. 3 is a diagram showing the magnetic field lines, represented by arrowheads, surrounding the magnet array of FIG. 2, when placed within a wellbore (Prior Art).
Figure 4:
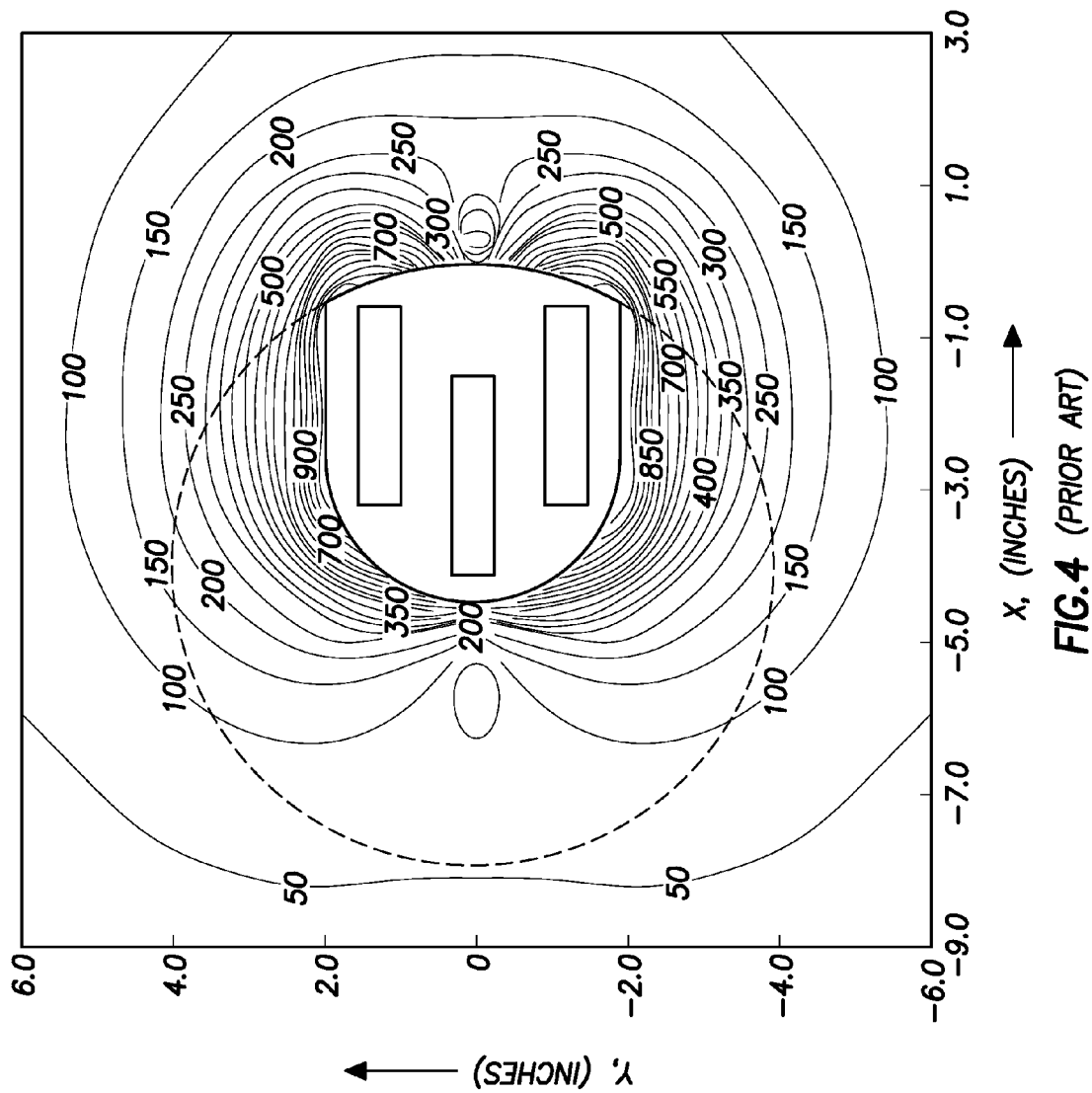
FIG. 4 is a diagram showing, in cross-section, magnetic field B.sub.0 equal-magnitude lines of the magnet array shown in FIGS. 2 and 3 (Prior Art).

Referring to FIGS. 2-4, by configuring the two N poles of magnets 24, 26 to point at the face 14 and the formation 12 lying beyond, magnet array 17 would appear at a substantial distance like a magnetic N pole. However, the reversed pole positioning of magnet 25 substantially alters the magnetic field at close and intermediate distances into formation 12. At intermediate distances, this preferred configuration of magnet array 17 produces an interesting and important field anomaly within a uniquely defined volume directly in front of the instrument face 14. As seen in greater detail in FIG. 4 there is a well-defined volume in which the magnetic field is substantially constant. This is the primary resonance region for NMR measurements and corresponds to the volume of investigation shown at 9 in FIG. 1. A plot of the direction of the static magnetic field in a plane perpendicular to the longitudinal axis of the instrument is shown in FIG. 3, wherein the dashed circle represents a wellbore having diameter of 8 inches (about 100 mm) in which the instrument (13 in FIG. 1) is placed in contact with the wellbore wall. FIG. 4 shows a plan view of static magnetic field amplitude for the same plane shown in FIG. 3. FIG. 5 shows the plan view of FIG. 3 with a line drawn through the zone having constant static magnetic field amplitude of 232.35 Gauss, which for the RF operating frequency of the instrument represents the zone in which NMR phenomena in hydrogen nuclei are excited.

As previously stated, while the invention is not limited to use with an instrument configured as shown in FIGS. 1 through 5, such instrument may facilitate implementing the invention because the zone of investigation (9 in FIG. 1) has a somewhat inhomogeneous static magnetic field. In the invention, certain characteristics of the RF pulses applied to the antenna (18 in FIG. 1) are selected such that FID signals can be measured. In one example, measuring FID signals after a plurality of magnetic reorientation RF pulses may enable measurement of $T_1$ properties of the subsurface formations using only one pulse sequence. An explanation of techniques according to the invention follows. In the following explanation, the terms "RF pulse", "RF magnetic pulse", "RF magnetic field pulse" and substantially similar terms are used synonymously with the act of passing a radio frequency current pulse through the antenna (18 in FIG. 1) so as to excite NMR phenomena in the formations adjacent to the instrument (13 in FIG. 1) or within the instrument. Passing the RF current pulse through the antenna has the effect of inducing a radio frequency magnetic field in the formations according to the dipole moment of the antenna and the amplitude and duration of the current pulse. Voltages induced in the antenna during times when detection circuits (not shown) are connected to the antenna are intended to correspond to electromagnetic field amplitude of such fields induced by NMR phenomena.

The NMR signal, M(t), measured after prepolarization of hydrogen nuclei in the static magnetic field and immediately after the application of a tipping (90 degree) RF magnetic pulse is the FID signal, and its amplitude with respect to time may be represented by the following expression:

$$M(t)=M_0\exp(-t/T_2^*) \tag{1}$$

where $M_0$ is the equilibrium magnetization and the FID signal decay time constant $T_2^*$ is given by the expression $$1/T_2^*=1/T_2'+\gamma\Delta B_0/2 \tag{2}$$

where $T_2$ is the spin-spin or transverse relaxation time, $\gamma$ is the gyromagnetic ratio of the excited hydrogen nuclei, $\Delta B_0$ is the magnetic field inhomogeneity, and $T_2'$ is the sample-induced inhomogeneity. The time constant characterizing sample-induced inhomogeneity is calculated to be 2.7 seconds at 60 Gauss field amplitude, which does not influence $T_2^*$ and therefore can be neglected.

The frequency bandwidth $\Delta v$ of a rectangularly shaped RF pulse is inversely proportional to the duration of the RF pulse. If the amplitude of the RF pulse is kept constant and the RF pulse duration is varied, the frequency bandwidth of the RF pulse is changed and correspondingly the magnetic field inhomogeneity ($\Delta B_0$ in Equation 2) in the volume of investigation is also varied. Therefore, the FID decay time constant should change with the RF pulse width. The frequency bandwidth within the volume of investigation is larger for smaller RF pulse duration, and correspondingly faster FID decay time $T_2^*$ should be observed. The magnetic field frequency bandwidth in the volume of investigation for a larger pulse duration is smaller, and therefore the FID decay time should be longer.

Figure 6:
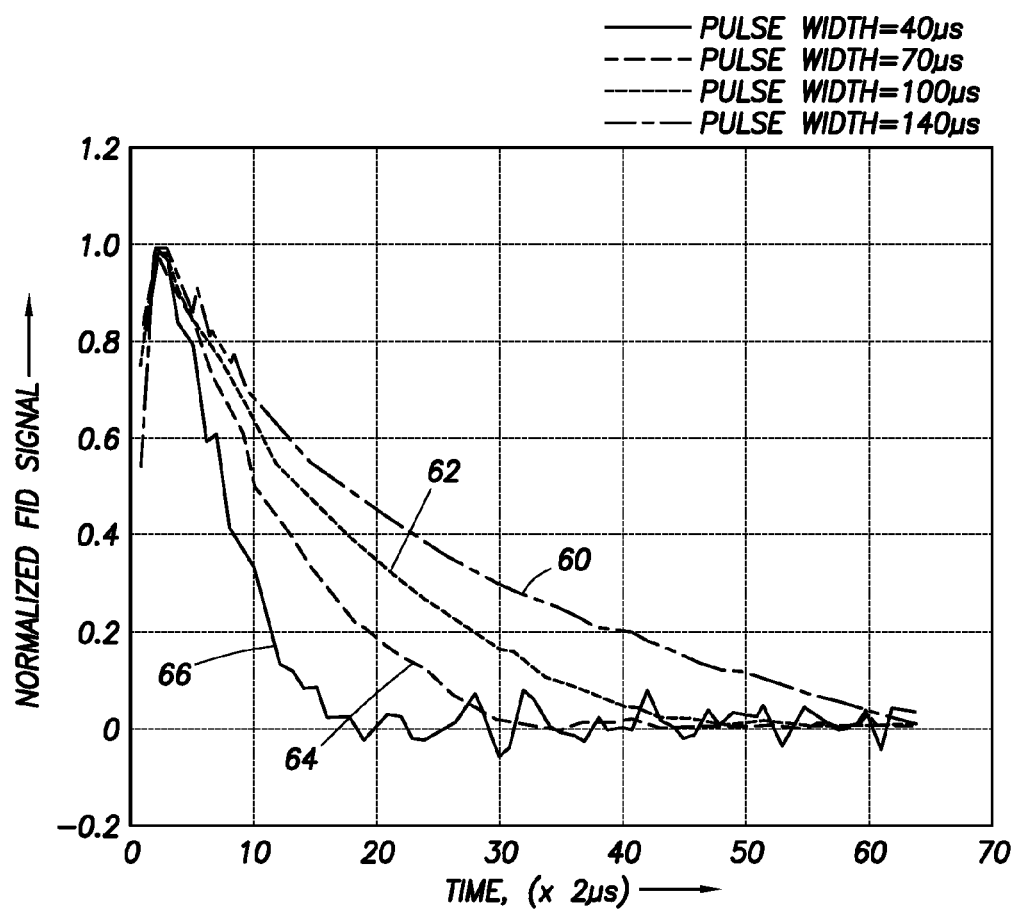
FIG. 6 shows test results of amplitude of a FID signal for various RF magnetic field pulse durations.

An experimental NMR signal apparatus was produced to test the above hypothesis. The apparatus included a RF signal test generator, test antenna, RF signal acquisition circuitry and a spectrum analyzer. In the test apparatus, a RF current pulse of selected duration was applied to the antenna. After a delay of five microseconds, the signal induced in the antenna, which is the FID signal, was measured. The normalized FID signal amplitude measured after each of a plurality of RF pulses of various durations is shown in FIG. 6. The FID signal measured after one RF pulse of duration of 40 microseconds is shown at curve 66. Corresponding FID signal amplitude curves are shown for RF pulse durations of 70, 100, and 140 microseconds as curves 64, 62 and 60, respectively in FIG. 6.

As is known in the art, the angular rotation of the nuclear spins by application of RF magnetic field at the Larmor frequency is related to the product of the duration and amplitude of the RF magnetic field pulse. In one example, a CPMG sequence used to make measurements of $T_2$ properties of the subsurface formations can be initiated with a tipping (90 degree) pulse having duration and amplitude selected to provide 90 degree spin reorientation. The duration of the 90 degree pulse may be lengthened, and the corresponding pulse amplitude can be reduced to maintain the effective reorienting angle caused by the RF pulse at 90 degrees. Reducing the amplitude and thereby decreasing the RF field bandwidth has the effect of reducing the magnetic field inhomogeneity in the volume of investigation such that the FID signal can be measured after the end of the 90 degree RF pulse. A sequence of 180 degree refocusing (inverting) RF pulses in a conventional CPMG sequence may follow after a selected interecho time (TE), wherein the spin echo amplitude after each refocusing pulse is measured. The spin echo amplitudes measured may be analyzed conventionally, such as to obtain $T_2$ distribution of the formation. Characteristics of the FID signal may be used to determine, for example, the porosity of the formation (12 in FIG. 1). Thus a modified CPMG sequence having a reduced-bandwidth 90 degree pulse and a plurality of refocusing pulses may be used to determine FID and $T_2$ properties of the formations (11, 12 in FIG. 1).

In another aspect, $T_1$ (longitudinal relaxation time) properties of the formations (11, 12 in FIG. 1) may be determined by measuring the FID signal in an inversion recovery or saturation recovery pulse sequence. A plurality of relatively small reorientation angle RF pulses is applied, each leading to a FID signal that is monitored. The reorientation angle caused by each of the RF pulses may be on the order of ten to forty degrees. The first such "small angle" reorientation pulse follows a magnetization inversion pulse (duration and amplitude selected to reorient the nuclear magnetic spins by 180 degrees). A time delay τ between each successive RF pulse may be selected to optimize the results obtained. As in the FID measurement technique described above, the duration of the reorientation pulses may be selected to provide relatively narrow bandwidth of the RF magnetic field, and the amplitude correspondingly reduced, to enhance the capability of measuring the FID signal following each small angle reorienting pulse.

A possible advantage of using small angle reorientation RF pulses is that after the application of each reorienting RF pulse, a substantial portion of nuclear magnetization still exists along the direction of the static magnetic field. Only a small portion of the nuclear magnetization is rotated into the plane transverse to the static magnetic field, and such magnetization is used for the observation of the NMR signal. Therefore, it is possible to repeat the application of another small angle reorientation RF pulse without having to wait for the return of nuclear magnetization along the direction of the static magnetic field.

It can be assumed that the transverse magnetization decays irreversibly during the delay time τ between pulses and there is substantially no interference on the succeeding FID signals. After the application of a number of small angle reorientation RF pulses, a dynamic equilibrium is established due to the increase in nuclear magnetization along the static magnetic field direction. The rotation of the magnetization by the reorientation or "flip" angle α and the steady state magnetization $M_{SA}$ for a saturation recovery sequence (a plurality of saturation reorienting RF pulses followed by small angle reorienting pulses after the delay time τ) are related by the expression:

$$M_{SA} = M_0 \frac{1 - \exp(-\tau/T_1)}{1 - \exp(-\tau/T_1)\cos(\alpha)} \quad (3)$$

The increase in nuclear magnetization after the saturation pulses as a function of the time of each small angle reorientation RF pulse is given by the expression:

$$M(n\tau) = M_{SA}\left(1 - \exp\left(-\frac{n\tau}{T_1^*}\right)\right) \quad (4)$$

where $M_{SA}$ represents the steady state magnetization, $M_0$ represents the equilibrium magnetization, nτ is the interval between the last saturation pulse and the (n+1) th low flip angle RF pulse, and $$\frac{1}{T_1^*} = \frac{1}{T_1} - \frac{\log(\cos(\alpha))}{\tau} \quad (5)$$

Figure 7:
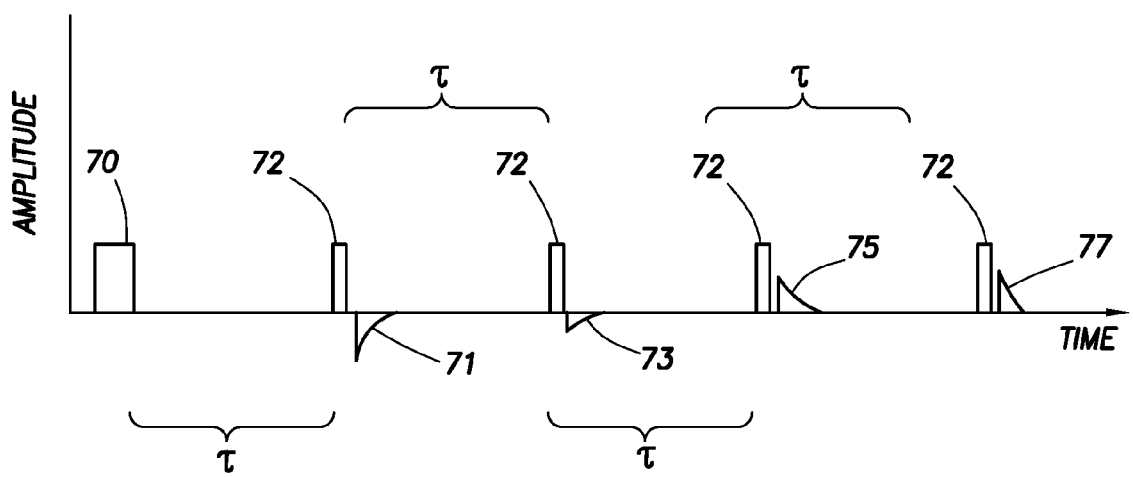
FIG. 7 shows an example pulse sequence for inversion recovery measurement of $T_1$ according to one aspect of the invention.

FIG. 7 shows an example of a single sequence of RF pulses and signal detection events for inversion recovery measurement of $T_1$ properties of the formation. After prepolarization of the nuclear magnetic spins of the hydrogen nuclei in the formation, a single inversion RF pulse 70 (flip angle of 180 degrees) is applied. After a selected delay time τ, a small reorientation angle RF pulse 72 is applied. The FID signal 71 is measured after the end of the small angle reorienting pulse 72. The foregoing reorienting pulse is repeated after each of a plurality of successive delay times τ, followed by measurement of the FID signal as shown at 73, 75 and 77.

Figure 8:
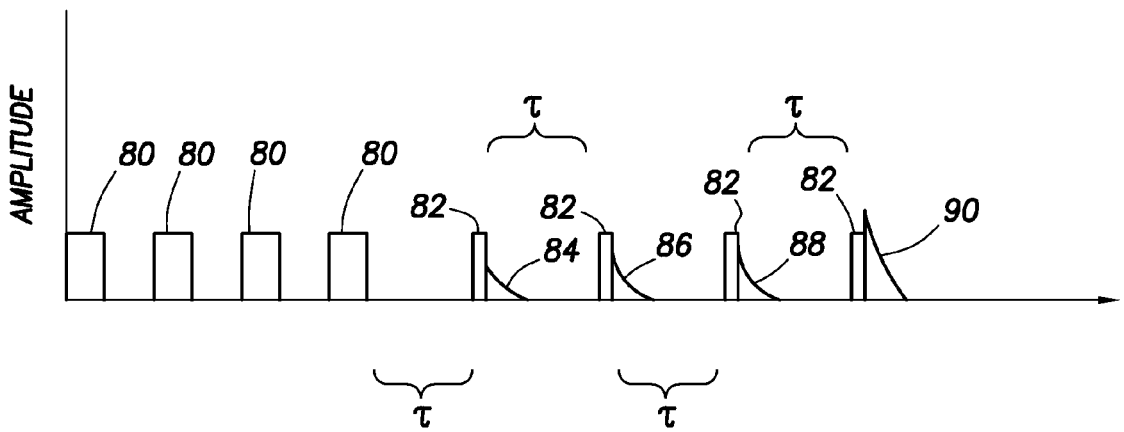
FIG. 8 shows an example pulse sequence for saturation recovery measurement of $T_1$ according to one aspect of the invention.

An example of a single sequence for saturation recovery determination of $T_1$ is shown in FIG. 8. After prepolarization of the hydrogen nuclei, a series of saturation RF pulses 80 is applied. After a delay time τ, a small reorientation angle RF pulse 82 is applied. The small reorientation angle RF pulse 82 is followed by measurement of the FID signal 84. After each of a plurality of delay times τ, a small reorientation angle RF pulse 82 is applied, and followed by measurement of the FID signal as shown at 86, 88 and 90. $T_1$ may be determined using equations 3 through 5 above. Using pulse sequences as explained above with reference to FIGS. 7 and 8 enables determining T1 properties of the subsurface formations using only a single sequence rather than multiple sequences spaced over a selected intersequence waiting time, as is required using prior art methods.

Figure 9:
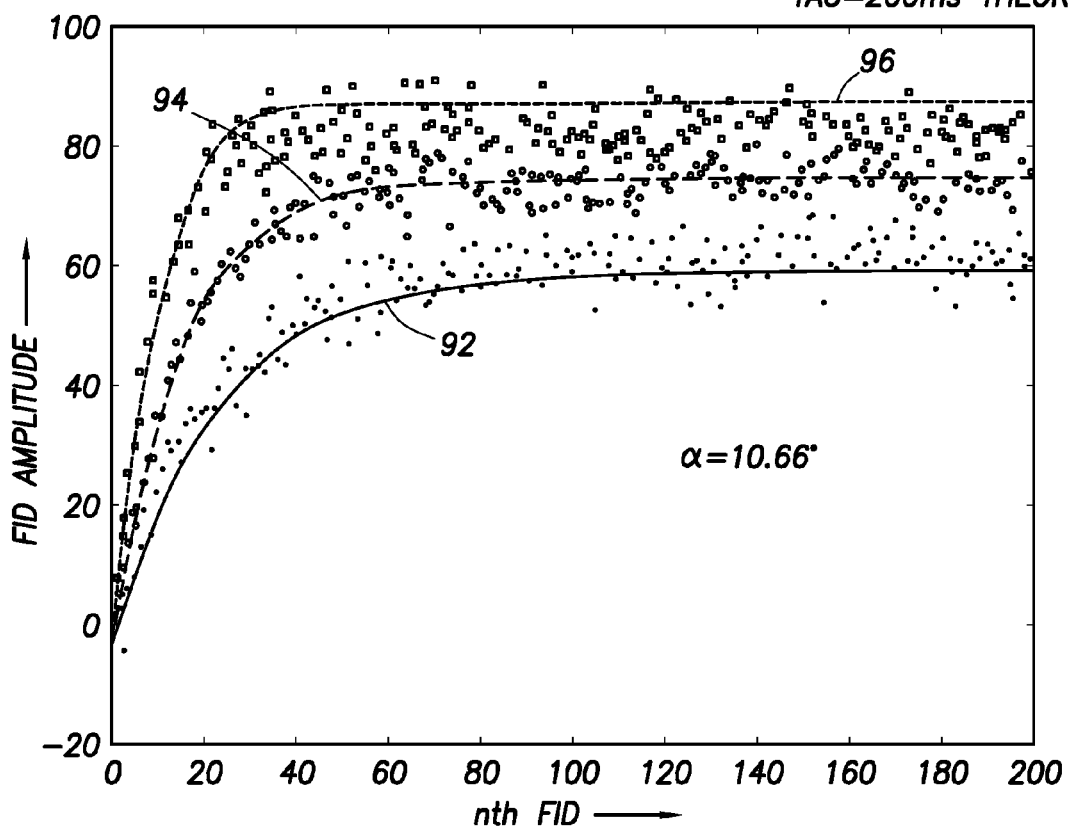
FIGS. 9 and 10 show graphs of test results of the pulse sequence of FIG. 8 using various reorientation angles and delay times between reorienting pulses.

Test results of a method for determining $T_1$ properties using water as a test substance are shown in FIG. 9 for a RF flip angle of 10.66 degrees. The FID signal amplitude measured after each of a plurality of RF pulses is shown graphically for delay time of 50 milliseconds at curve 92 and its associated data points, for delay time of 100 milliseconds at curve 94 and its associated data points, and for delay time of 200 milliseconds at curve 96 and its associated data points.

Figure 10:
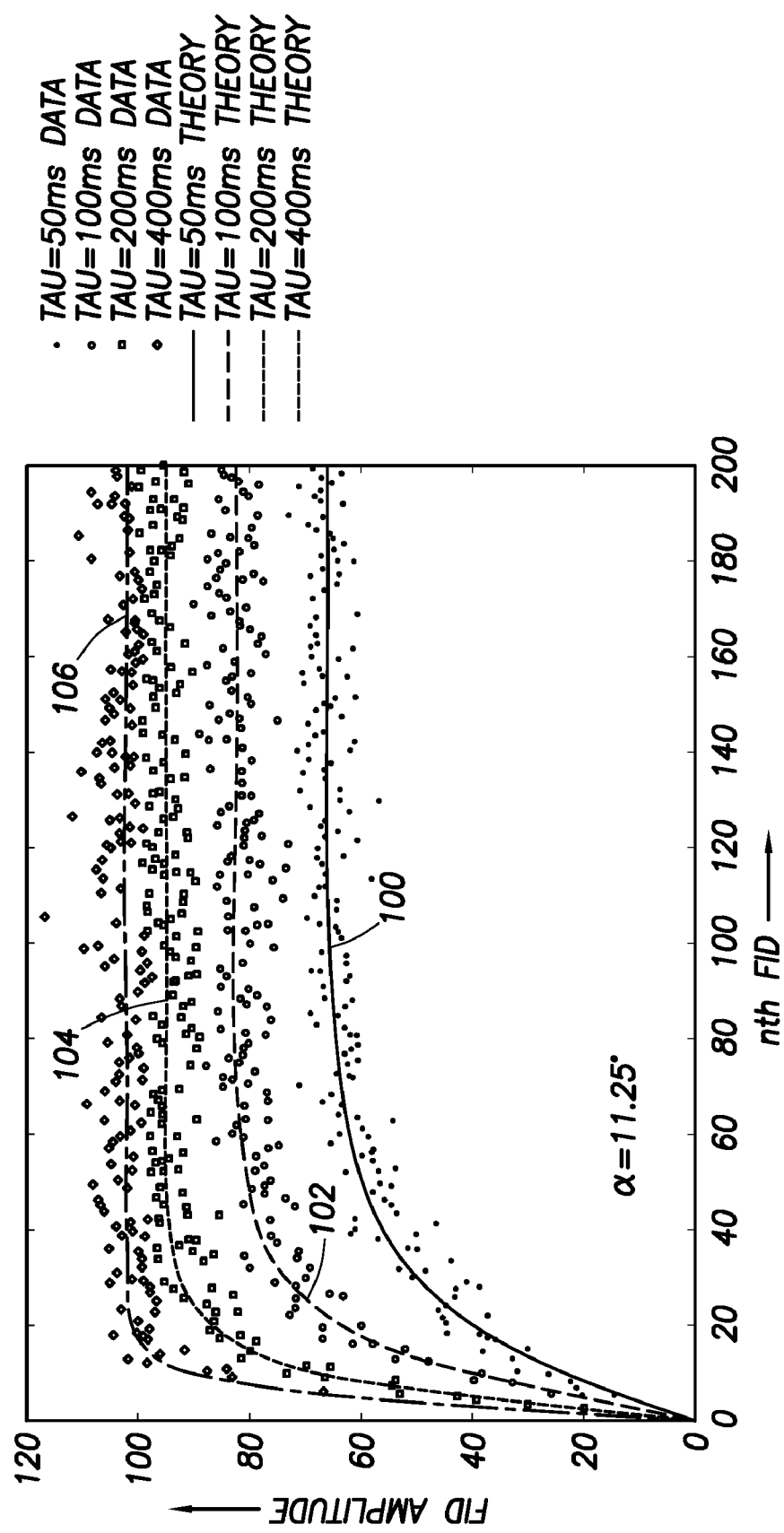

Corresponding test results are shown in FIG. 10 for the RF flip angle of 11.25 degrees. The results shown in FIG. 10 are for delay times, respectively, of 50 milliseconds at curve 100, 100 milliseconds at curve 102, 200 milliseconds at curve 104, and 400 milliseconds at curve 106.

Methods according to the invention enable determining free induction decay amplitude for wellbore logging and parameters determinable therefrom. Methods according to the invention also enable determining longitudinal relaxation time of earth formations in one measurement pulse sequence without the need for measuring multiple pulse sequences with waiting times therebetween. Methods according to the invention may also be used to determine self diffusion constant of formations and the fluids therein.

The foregoing methods are described as being implemented by a well logging instrument that makes measurements of formation properties from within a wellbore drilled through the formations. It is within the scope of this invention to perform similar measurements on samples of fluid withdrawn from the formations. Accordingly, in another aspect of the invention, a sample of fluid is withdrawn from the formation, and any of the above methods may be performed in substantially the same manner as on the formations themselves. One device for withdrawing a sample of fluid from the formations is described in U.S. Pat. No. 7,036,362 issued to Haddad et al. and incorporated herein by reference. Components disclosed above for inducing static and RF magnetic fields, and detecting the NMR signals, may be included in a device such as described in the '362 patent for performing the above described NMR methods on samples of fluid withdrawn from the formation by such instrument.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method to determine a property of a material in a sample volume using a free induction decay signal obtained using a downhole logging tool, comprising:
   inducing a static magnetic field in the sample volume using the downhole logging tool;
   inducing a tipping radio frequency magnetic field in the sample volume using the downhole logging tool, the tipping radio frequency magnetic field having parameters selected to minimize the contribution of inhomogeneity in the static magnetic field to a free induction decay time;
   detecting the free induction decay signal from the sample volume using the downhole logging tool; and
   determining the property of the material using the free induction decay signal.

2. The method of claim 1 further comprising:
   after a delay time after inducing the tipping radio frequency magnetic field, inducing a refocusing radio frequency magnetic field in the sample volume; and
   detecting at least one spin echo resulting from inducing the refocusing radio frequency magnetic field.

3. The method of claim 2 further comprising repeating inducing the refocusing radio frequency magnetic field and detecting a spin echo thereafter for a selected number of times.

4. The method of claim 3 wherein the property comprises transverse relaxation time of fluid in pore spaces of a porous medium in the sample volume.

5. The method of claim 3 wherein the property comprises self diffusion constant of fluid in pore spaces of a porous medium in the sample volume.

6. The method of claim 3 wherein the property comprises longitudinal relaxation time of fluid in pore spaces of a porous medium in the sample volume.

7. The method of claim 2 wherein the refocusing radio frequency magnetic field has parameters selected to substantially invert spins of nuclei in the sample volume.

8. The method of claim 1 wherein the tipping radio frequency magnetic field has parameters selected to reorient spins of nuclei in the sample volume by a first selected angle.

9. The method of claim 8 wherein the first selected angle is substantially ninety degrees.

10. The method of claim 1 wherein the property comprises fractional volume of pore space of a porous medium.

11. The method of claim 1 wherein the sample volume is disposed in formations surrounding a wellbore drilled through the Earth's subsurface.

12. The method of claim 1 wherein the sample volume is disposed in a selected volume of fluid withdrawn from subsurface Earth formations.

13. A method to determine at least one property of materials in a sample volume using a free induction decay signal obtained using a downhole logging tool, comprising:
   inducing a static magnetic field in the sample volume using the downhole logging tool;
   inducing a tipping radio frequency magnetic field in the sample volume using the downhole logging tool, the tipping radio frequency magnetic field having parameters selected to orient nuclear magnetic spins by a first selected angle;
   after a delay, inducing a reorienting radio frequency magnetic field in the sample volume using the downhole logging tool, the reorienting radio frequency magnetic field having parameters selected to reorient magnetic spins by a second selected angle and to minimize the contribution of inhomogeneity in the static magnetic field to a free induction decay time;
   detecting a free induction decay signal from the sample volume using the downhole logging tool;
   repeating inducing the reorienting radio frequency magnetic field and detecting the free induction decay signal using the downhole logging tool to produce a plurality of free induction decay signals; and
   determining the at least one property from at least one of the free induction decay signals.

14. The method of claim 13 wherein the tipping radio frequency magnetic field has parameters selected to substantially invert the nuclear magnetic spins.

15. The method of claim 13 wherein the tipping radio frequency magnetic field comprises a plurality of saturation radio frequency magnetic fields.

16. The method of claim 13 wherein the second selected angle is substantially within a range of ten to forty degrees.

17. The method of claim 13 further comprising determining the at least one property of the materials in the sample volume from a single measurement pulse sequence.

18. The method of claim 13 wherein the sample volume is disposed in formations surrounding a wellbore drilled through the Earth's subsurface.

19. The method of claim 13 wherein the sample volume is disposed in a selected volume of fluid withdrawn from subsurface Earth formations.

* * * * *